United States Patent [19]

Spear et al.

[11] Patent Number: Plant 7,636

[45] Date of Patent: Aug. 27, 1991

[54] MUSHROOM PLANT NAMED BROWN HYBRID X618

[75] Inventors: Mark C. Spear; Rebecca Miller, both of Cabot, Pa.

[73] Assignee: Sylvan Spawn Laboratory, Inc., Kittanning, Pa.

[21] Appl. No.: 363,095

[22] Filed: Jun. 8, 1989

[51] Int. Cl.[5] ..... A01H 15/00

[52] U.S. Cl. ..... Plt./89

[58] Field of Search ..... Plt./89; 800/2, DIG. 8, 800/DIG. 21; 47/1.1

[56] References Cited

U.S. PATENT DOCUMENTS 4,608,775 9/1986 Elliott et al. ..... 47/1.1

*Primary Examiner*—James R. Feyrer

*Attorney, Agent, or Firm*—Reed Smith Shaw & McClay

[57] ABSTRACT

A new and unique variety of brown mushroom is described. It exhibits (1) high production yields when compared to common commercial varieties, (2) excellent Verticillium disease resistance and (3) a distinct electrophoretic isozyme pattern.

4 Drawing Sheets

FIELD OF THE INVENTION

The present invention relates to a new and unique variety of mushroom plant of *Agaricus bisporus* (Lange) Imbach [=*Agaricus brunnescens* Peck].

BACKGROUND OF THE INVENTION

Due to the endogenous automictic nuclear behavior of the cultivated mushroom as described by Kerrigan in *Evolution and Agaricus bisporus,* Ph.D. disseration (1989), University of California (Santa Barbara), few new and unique varieties of cultivated mushroom have become commercially available. Those that have become available and that have been used commercially were developed primarily to achieve high production yields and a bright, white color. As a result, nearly all commercially produced mushrooms are genetically very similar as described by Royce and May in *Mycologia* 74:93–102 (1982).

A consequence of the genetic similarity of most commercially-produced muchrooms is that they are susceptible to diseases caused by common pathogens. The diseases can have a devastating impact on the yield and quality of a mushroom harvest. Verticillium disease, also called dry bubble and Verticillum spot, is one of the most troublesome of these diseases. It is caused by the fungus *Verticillium fungicola* (Preuss) *Hessebr. var. fungicola* as described by Gams and Zaaryen, *Neth. J. Pl. Path.* 88:57–58 (1982).

Typically, Verticillium disease is controlled with hygienic cultural practices and/or fungicides. Currently, the most effective commercial fungicide approved and labeled for such control is zinc ethylene bisdithiocarbamate known to the trade as Zineb TM. However, the Environmental Protection Administration has suspended its approval for the registration of this material, and it can no longer be used in the United States. Without it, many mushroom farms using conventional mushroom varieties will most likely not be able to sustain the yield and quality levels which they need to remain economically viable.

Consequently, the incorporation of disease resistance into the genetic makeup of mushroom varieties represents an efficient, cost-effective and environmentally responsible solution to the problem, and a need for such a disease resistant mushroom exists.

SUMMARY OF THE INVENTION

The present invention is a new and distinct variety of mushroom characterized particularly by its greater resistance to Verticillium disease when compared to commercially available lines 56B and 381 and by its unique electrophoretic isozyme phenotype. This novel and distinct variety of mushroom is identified as Brown Hybrid X618.

BRIEF DESCRIPTION OF THE FIGURES

FIG. 2 illustrates the disease severity protocol used to evaluate resistance of Brown Hybrid X618 and presently commercially available varieties of mushrooms to Verticillium disease.

DETAILED DESCRIPTION OF THE INVENTION

The present invention is a new and distinct variety of the commonly cultivated white mushroom *Agaricus bisporus* (Lange) Imbach [=*Agaricus brunnescens* Peck]. It is referred to by the variety name of X618 and was produced in the breeding program of Sylvan Spawn Laboratory, Inc., Kittanning, Pa.

In mushroom breeding, compatible breeding lines, called homokaryons, are roughly analogous to sperm and egg. They are derived from parent varieties and must be combined to produce a hybrid.

The X618 variety resulted from the hybridization of two compatible homokaryons. The varieties from which these homokaryons were derived are called the parent varieties. These are Sylvan 381 and Somycel 56B. Sylvan 381 is a commercially available, high-yielding white mushroom which is susceptible to Verticillium disease. Somycel 56B is a brown mushroom which is available from The Pennsylvania State University (PSU) Mushroom Culture Collection. It is used commercially, is low-yielding and somewhat resistant to Verticillium disease.

Figure 1:
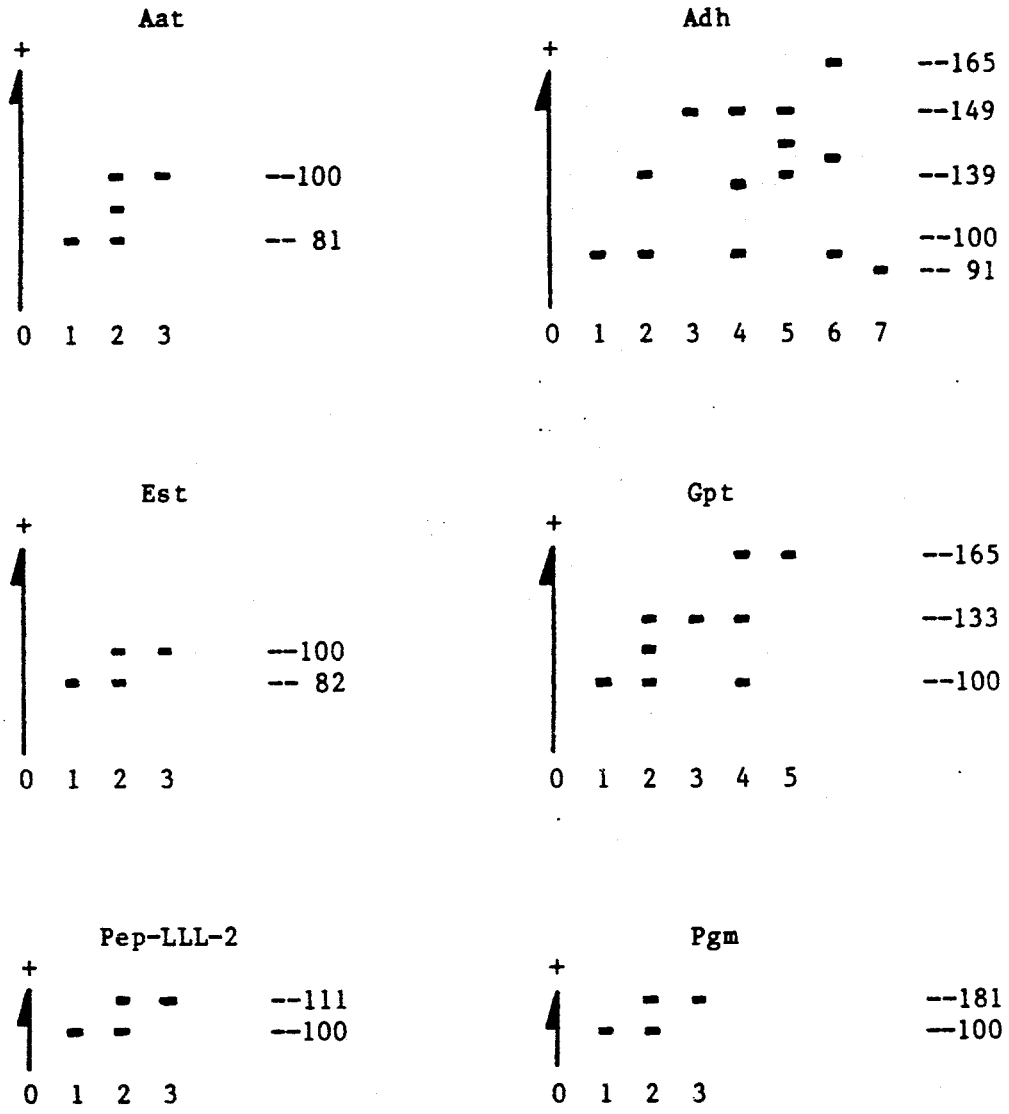
FIG. 1 illustrates the isozyme patterns used to characterize the claimed variety of mushroom identified as Brown Hybrid X618.

The homokaryons (identified as 381-907 and 56B-4186) were typed by isozyme electrophoresis as taught by Royce and May in *Mycologia*, 74:93–102 (1982), the disclosure of which is incorporated herein by reference. The hybridization of X618 was achieved by dual culture of the homokaryons on agar by well-known methods. The genetic markers for these homokaryons, for the parent strains 381 and 56B and for X618 hybrid are set forth in Table 1. Table 1 indicates that X618 contains genetic material from each of the parent lines and is, therefore, a true hybrid of the parent varieties. FIG. 1 depicts the isozyme patterns of X618 which are referred to in Table 1. The X618 hybrid is genetically unique and its isozyme pattern is identifiable and distinct from that of any commercial or published variety.

X618 is a tan to brown mushroom. The coloration is even to scrobiculate. Chroma meter readings of the mature pileus range on the CIE (Commission Internationale de l'Eclairage) scale from Yxy of 43.83, 0.3777, 0.3660, to a Yzy of 34.49, 0.3811, 0.3640, readings which correspond to the Royal Horticultural Society Colour Charts selections near 159A and 172D. The stipe is always bright white. Cap color tends to lighten later in the cropping cycle or when grown in absolute darkness. The tissue does not bruise or discolor upon injury. The cap margin is incurved. If the mushroom is permitted to become over-mature the cap margin becomes straight or flaring and the partial veil remains attached to the stipe.

The pileus of X618 is 20–150 mm in diameter, planar to hemispherical and slightly umbillicate. The cuticle is smooth appressed fibrillose and not viscid. Gill trama are irregularly parallel and divergent at the tip. Gills are closely spaced and the basidia are clavate and mostly two-spored. Pleurocystidia are absent. Pileus tramal hyphae are 22–32 μm long and 11–14 μm wide. Pileus cutical hyphae are 10–12 μm in diameter and 23–27 μm in length. Spores are approximately 9 μm in length and 6 μm in diameter. They are ovate in shape and without a germ pore. Spore color is purple-brown to black.

The X618 has a richer flavor than current white commercial mushroom varieties and is more firm and crunchy.

Evaluations of X618 were conducted to assess its production yield potential and its resistance to Verticillium. Small scale production tests were performed in Sylvan Spawn Laboratory, Inc.'s mushroom cultivation facilities at Cabot, Pa. Larger scale tests were performed in the facilities of Moonlight Mushrooms, Inc. at Worthington, Pa.

After the new variety was established, it was reproduced and maintained asexually by standard techniques in the Sylvan Spawn Laboratories facilities at Cabot and Kittanning, Pa. using standard agar and grain media.

The yield test results are summarized in Table 2. The yield characteristics of X618 are compared with a group of commercial mushroom varieties identified in Table 2 which were selected as representing the majority of the genetic variability which is presently available in commercial mushroom varieties. The class designation used is that described by Royce and May in *Mycologia* 74:93–102 (1982), the disclosure of which is incorporated herein by reference. Included in the comparisons are the parent strains of X618. The comparisons were made at three levels of Verticillium pathogen exposure (0, 100 and 1000 Verticillium spores added per pot). As measured in grams of mushrooms produced per test unit over a seven day period, Table 2 indicates that the yields of X618 compare favorably with the other varieties at the 0 exposure level and are better at the 100 and 1000 exposure levels than the preexisting varieties of mushrooms.

Table 2 further displays the results of two tests for disease resistance. The tests measure the occurrences of certain characteristic symptoms of Verticillium disease. These symptoms are the (1) appearance of necrotic lesions on the cap and stem of the mushrooms and (2) growth on mushroom beds of "bubbles"—hypertrophied mushroom primordia—where normal mushrooms should be. The comparative measurements for the first test (indicated as "Disease") are called "disease severity ratings." The ratings numbers correspond to proportions of total mushrooms in test crops which exhibit all symptoms. FIG. 2 describes the severity rating scale. The comparative measurement for the second test (indicated as "Bubbles") is the count of occurrences of the hypertrophied mushroom primordia in each production test unit at each pathogen exposure level. Both measures indicate that X618 has significantly higher resistance to Verticillium disease than do the comparison varieties of preexisting commercial varieties of mushrooms.

Figure 3:
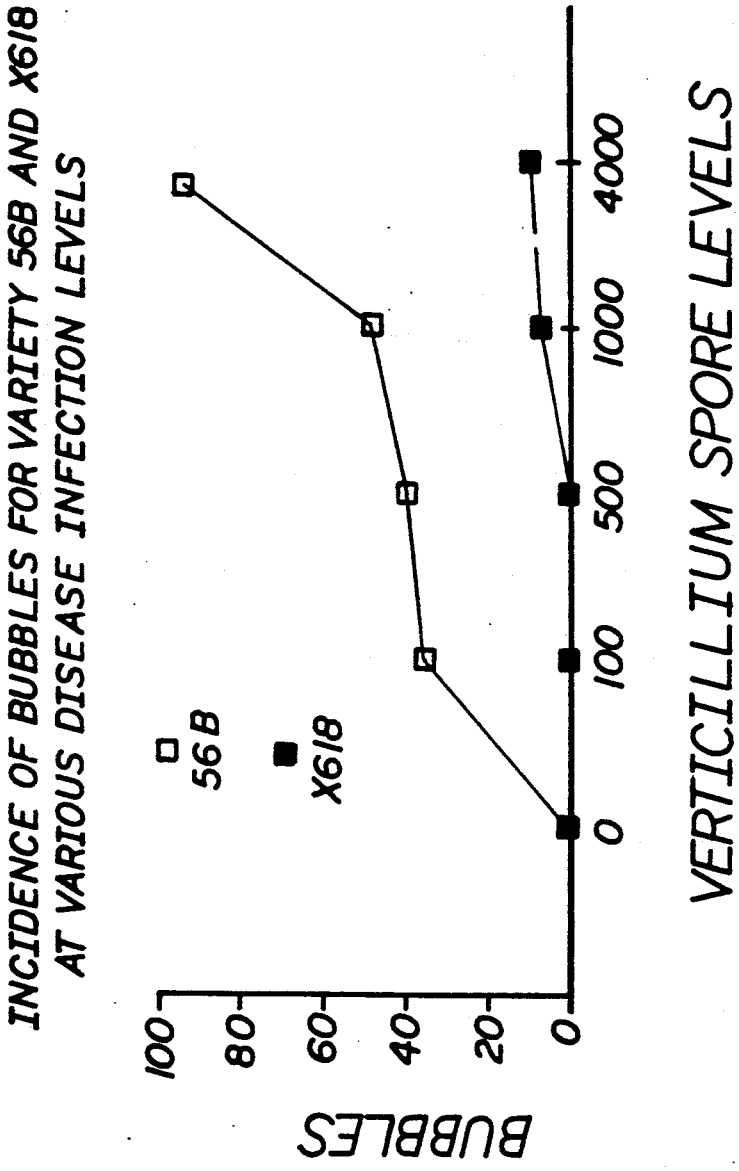
FIG. 3 illustrates the incidence of bubbles at various Verticillium disease infection levels of Brown Hybrid X618 as compared to commercially available line 56B. The bubbles referred are growth on mushroom beds of hypertrophied mushroom primordia, i.e., "bubbles", where normal mushrooms should have grown.
Figure 4:
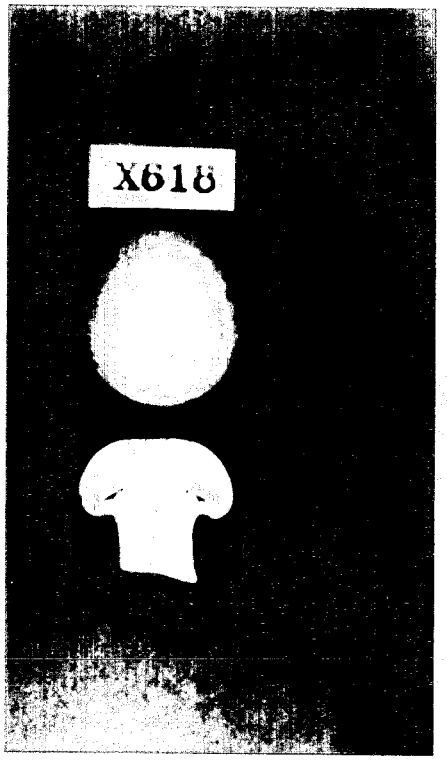
FIG. 4 is a photograph showing two views of the X618 mushroom variety of the subject invention.
Figure 4:
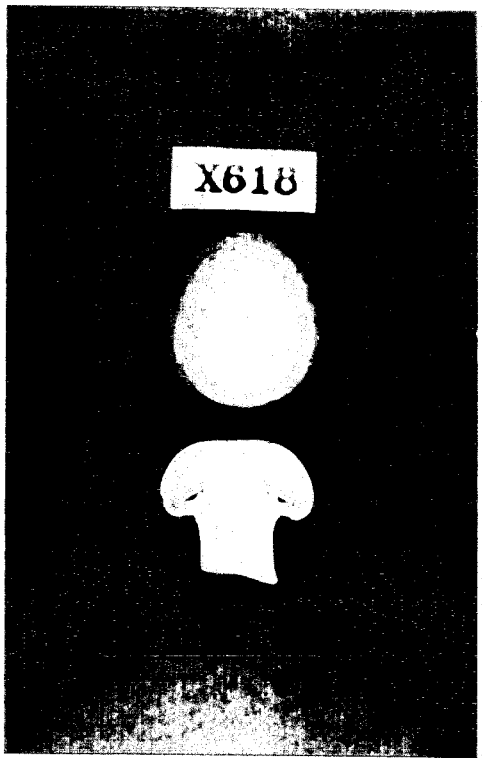

Table 3 also displays the results of two tests for disease resistance. The results are similar to these which are reported in Table 2, except that X618 was compared only to its Somycel 56B parent, and it was compared at additional Verticillium disease exposure levels. As in the Table 2 test, both measures (bubbles and disease severity ratings) indicate that X618 has significantly higher resistance to Verticillium disease than its somewhat disease resistant parent. FIG. 3 displays the results of the bubbles measurement test reported in Table 3 in graphical form.

TABLE 1

Phenotypes of Alleles Found In X618, Its Parent Homokaryons and Its Parent Varieties

| | BIOCHEMICAL LOCI | | | | | |
|---|---|---|---|---|---|---|
| Variety | AAT | ADH | EST | GPT | Pep-2 | PGM |
| 381 | 100/100 | 100/149 | 100/100 | 100/100 | 100/111 | 100/181 |
| 56B | 81/100 | 149/149 | 82/82 | 100/133 | 100/111 | 100/181 |
| 381-907 | 100 | 149 | 100 | 100 | 111 | 100 |
| 56B-4186 | 81 | 149 | 82 | 133 | 111 | 181 |
| X618 | 81/100 | 149/149 | 82/100 | 100/133 | 111/111 | 100/181 |

TABLE 2

Mushroom Yields in Grams, Disease Severity Ratings and Incidence of Bubbles For Various Mushroom Varieties At Various Disease Infection Levels

| | VARIETIES | | | | |
|---|---|---|---|---|---|
| Variety | X618 Hybrid | S100 Hybrid | S110 Hybrid | Mc310 | Mc266 |
| Type | Brown | Off White | Off White | White | White |
| Class | None | 11 | 11 | 2 | 22 |
| From | Sylvan | Sylvan | Sylvan | PSU | PSU |

0 Verticillium spores added per pot

TABLE 2-continued

Mushroom Yields in Grams, Disease Severity Ratings and Incidence of Bubbles For Various Mushroom Varieties At Various Disease Infection Levels

| | | | | | |
|---|---|---|---|---|---|
| Yield | 277 | 295 | 163 | 132 | 313 |
| Severity Rating | 0 | 0 | 0 | 0 | 0 |
| Bubbles | 0 | 1 | 0 | 0 | 0 |
| 100 Verticillium spores added per pot | | | | | |
| Yield | 363 | 236 | 158 | 86 | 181 |
| Severity Rating | 1 | 3 | 3 | 3 | 4 |
| Bubbles | 0 | 3 | 50+ | 33 | 47 |
| 1000 Verticillium spores added per pot | | | | | |
| Yield | 336 | 66 | 227 | 54 | 299 |
| Severity Rating | 2 | 5 | 5 | 5 | 5 |
| Bubbles | 7 | 50+ | 50+ | 50 | 98 |

| | VARIETIES | | | |
|---|---|---|---|---|
| Variety | S8132 | S671 | 56B | S381 |
| Type | Off White | Golden White | Brown | Hybrid White |
| Class | 31 | 19 | 27 | 11 |
| From | Sylvan | Sylvan | Somycel | Sylvan |
| 0 Verticillium spores adder per pot | | | | |
| Yield | 168 | 227 | 127 | 267 |
| Severity Rating | 0 | 0 | 0 | 0 |
| Bubbles | 0 | 0 | 0 | 0 |
| 100 Verticillium spores added per pot | | | | |
| Yield | 217 | 145 | 136 | 349 |
| Severity Rating | 3 | 3 | 3 | 4 |
| Bubbles | 77+ | 65 | 32 | 30 |
| 1000 Verticillium spores added per pot | | | | |
| Yield | 190 | 77 | 136 | 308 |
| Severity Rating | 5 | 5 | 4 | 5 |
| Bubbles | 132 | 76 | 35 | 50+ |

TABLE 3

Incidence of Bubbles For Variety 56B and X618 At Various Disease Infection Levels

| Number of Verticillium Spores | VARIETY 56B Bubbles | 56B Severity Rating | X618 Bubbles | X618 Severity Rating |
|---|---|---|---|---|
| 0 | 0 | 0 | 0 | 0 |
| 100 | 37 | 4 | 0 | 0 |
| 500 | 41 | 4 | 0 | 2 |
| 1000 | 50 | 4 | 4 | 3 |
| 4000 | 96 | 5 | 7 | 3 |

What is claimed is:

1. A new and distinct variety of mushroom substantially as shown and described, characterized particularly as to novelty by its greater resistance to Verticillium disease when compared to commercially available lines 56B and 381 and by its unique electrophoretic isozyme phenotype.

* * * * *

REPRESENTS THE ISOZYME PATTERNS FOUND IN AGARICUS BISPORUS

DISEASE SEVERITY RATING PROTOCAL

| RATING | MEANING | APPROXIMATE COUNTS |
|---|---|---|
| 0 = | NO SIGNS OF INFECTION | |
| 1 = | NON ECONOMIC IMPORTANCE, | 1-3 % OF MUSHROOMS AFFECTED |
| 2 = | NOTICEABLE ECONOMIC IMPACT, | 4-10% AFFECTED |
| 3 = | HEAVY DISEASE INFECTION, | 11-25% AFFECTED |
| 4 = | GRAVE ECONOMIC IMPACT, | 26-50% AFFECTED |
| 5 = | CROP FAILURE, NOT HARVESTED | 51-100 % AFFECTED |

FIG. 2